United States Patent
Conley (10) Patent No.: US 10,761,078 B2
(45) Date of Patent: Sep. 1, 2020

(54) APPARATUS AND METHODS FOR TESTING OIL SEPARATION FROM GREASE

(71) Applicant: Lincoln Industrial Corporation, St. Louis, MO (US)

(72) Inventor: Paul G. Conley, St. Charles, MO (US)

(73) Assignee: Lincoln Industrial Corporation, St. Louis, MO (US)

( * ) Notice: Subject to any disclaimer, the term of this patent is extended or adjusted under 35 U.S.C. 154(b) by 189 days.

(21) Appl. No.: 16/120,545

(22) Filed: Sep. 4, 2018

(65) Prior Publication Data

US 2020/0072811 A1 Mar. 5, 2020

(51) Int. Cl.
| | |
|---|---|
| *G01N 33/28* | (2006.01) |
| *G01N 19/00* | (2006.01) |
| G01N 35/00 | (2006.01) |
| G01N 33/30 | (2006.01) |

(52) U.S. Cl.
CPC ......... *G01N 33/2823* (2013.01); *G01N 19/00* (2013.01); *G01N 33/30* (2013.01); *G01N 2035/00465* (2013.01)

(58) Field of Classification Search
CPC .... G01N 19/00; G01N 33/30; G01N 33/2823; G01N 2035/0465; G01N 2035/0495; C01M 175/00; C01M 175/02
See application file for complete search history.

(56) References Cited

U.S. PATENT DOCUMENTS

| | | | | | |
|---|---|---|---|---|---|
| 1,665,933 | A | * | 4/1928 | Rodman | G01N 33/30 73/53.05 |
| 1,741,696 | A | * | 12/1929 | Greenhalgh | C10M 175/00 196/46.1 |
| 1,868,917 | A | * | 7/1932 | Rodman | C10M 175/00 184/6.21 |
| 2,063,903 | A | * | 12/1936 | Bijur | F16N 7/385 184/7.3 |
| 2,313,896 | A | * | 3/1943 | Scheble | C10M 175/00 210/167.02 |
| 3,045,471 | A | * | 7/1962 | Chapman | G01N 33/30 73/10 |
| 3,946,593 | A | * | 3/1976 | Ruget | G01N 33/30 73/10 |
| 4,272,359 | A | * | 6/1981 | Owen | C10B 53/00 196/46 |
| 4,466,271 | A | * | 8/1984 | Geromiller | G01N 19/02 73/10 |

(Continued)

FOREIGN PATENT DOCUMENTS

| | | | | |
|---|---|---|---|---|
| DE | 19739659 A1 | * | 3/1999 | ............ G01N 33/30 |
| DE | 102010008826 A1 | * | 3/2011 | ...... C10M 175/0058 |

*Primary Examiner* — David J Bolduc
(74) *Attorney, Agent, or Firm* — Stinson LLP (57) ABSTRACT

A grease testing device for testing oil separation from a grease sample includes a container defining a grease compartment for holding the grease sample. A grease shearer is at least partially positioned in the grease compartment and moves in the grease compartment to shear the grease sample in the grease compartment. A motor is operatively connected to the grease shearer to move the grease shearer in the grease compartment to shear the grease sample. A drain is arranged with respect to the grease compartment to receive oil separated from the grease sample from the grease compartment.

20 Claims, 6 Drawing Sheets

(56) References Cited

U.S. PATENT DOCUMENTS

| | | | | |
|---|---|---|---|---|
| 5,553,870 | A * | 9/1996 | Czekansky | B60B 35/121 |
| | | | | 277/559 |
| 5,679,883 | A * | 10/1997 | Wedeven | G01N 3/56 |
| | | | | 73/10 |
| 8,904,852 | B2 * | 12/2014 | Wollny | G01N 11/142 |
| | | | | 73/54.27 |
| 9,671,319 | B1 * | 6/2017 | Batten | G01N 1/2035 |
| 2001/0001198 | A1 * | 5/2001 | Sherman | C10M 175/0033 |
| | | | | 208/181 |
| 2005/0095718 | A1 * | 5/2005 | Wollenberg | B01J 19/0046 |
| | | | | 436/60 |
| 2006/0054550 | A1 * | 3/2006 | Batten | B01D 17/0202 |
| | | | | 210/523 |
| 2007/0032964 | A1 * | 2/2007 | Kaldor | G01N 33/30 |
| | | | | 702/25 |
| 2008/0078238 | A1 * | 4/2008 | Stockhammer | G01N 33/30 |
| | | | | 73/53.05 |
| 2008/0113886 | A1 * | 5/2008 | Kinker | C10M 129/38 |
| | | | | 508/111 |
| 2008/0149553 | A1 * | 6/2008 | Sowerby | B01D 17/005 |
| | | | | 210/301 |
| 2009/0183580 | A1 * | 7/2009 | Wurzbach | G01N 1/14 |
| | | | | 73/864.14 |
| 2013/0152674 | A1 * | 6/2013 | Noordover | G01N 33/30 |
| | | | | 73/53.05 |
| 2013/0279835 | A1 * | 10/2013 | Akita | F16C 33/102 |
| | | | | 384/279 |
| 2014/0225332 | A1 * | 8/2014 | Baart | F16C 33/7876 |
| | | | | 277/549 |
| 2016/0319216 | A1 * | 11/2016 | Hutchenson | C10M 175/0083 |
| 2018/0292465 | A1 * | 10/2018 | Osara | G01M 5/0033 |

\* cited by examiner

APPARATUS AND METHODS FOR TESTING OIL SEPARATION FROM GREASE

FIELD

The present disclosure generally relates to apparatus and methods for testing oil separation from grease.

BACKGROUND

Lubricating greases are used to prevent metal-on-metal contact in moving parts, such as bearings. Generally, a grease is made of 70-95% oil, 3-30% thickener and 0-10% additives. The oil provides lubrication by forming a thin hydrodynamic film between the moving parts to prevent the moving parts from directly contacting one another. The thickener includes solid particles or fibers which hold the oil. Additives enhance or suppress certain grease qualities.

Oil separation or bleed out occurs when the oil is no longer held by the thickener, which reduces the lubrication qualities of the grease. Previous methods for determining oil separation from grease included the Standard Test Method for Oil Separation from Lubricating Grease by Centrifuging (Koppers Method—ASTM D4425) and the Standard Test Method for Oil Separation from Lubricating Grease (Conical Sieve Method—ASTM D6184) which subject a grease sample to centrifugal forces and higher temperatures, respectively, to test the oil separation from the grease sample.

Different types of greases can be combined to create a grease combination. However, not all greases are compatible with one another and incompatible grease combinations can lead to ineffective lubrication and damage of the lubricated components. Moreover, incompatible grease types may clog up the pumps and valves of a lubrication system, damaging the system and preventing the system from distributing the grease.

SUMMARY

In one aspect, a grease testing device for testing oil separation from a grease sample, comprises a container defining a grease compartment for holding the grease sample, a grease shearer at least partially positioned in the grease compartment and configured to move in the grease compartment to shear the grease sample in the grease compartment, a motor operatively connected to the grease shearer to move the grease shearer in the grease compartment to shear the grease sample, and a drain arranged with respect to the grease compartment to receive oil separated from the grease sample from the grease compartment.

In another aspect, a method for testing a grease for oil separation comprises providing a first grease sample of a first grease type in a grease compartment, moving a grease shearer in the grease compartment for a first shearing duration to shear the first grease sample in the grease compartment, collecting oil separated from the first grease sample from the grease compartment, and comparing an amount of the collected oil to an amount of the first grease sample to determine a first oil separation value of the first grease sample.

The above summary is provided to introduce a selection of concepts in simplified form that are further described below in the Detailed Description. The summary is not intended to identify key features or essential features of the claimed subject matter, nor is it intended to be used as an aid in determining the scope of the claimed subject matter. Other objects and features will be in part apparent and in part pointed out hereinafter.

BRIEF DESCRIPTION OF THE DRAWINGS

Corresponding parts are indicated by corresponding reference numbers throughout the drawings.

DETAILED DESCRIPTION

Figure 1:
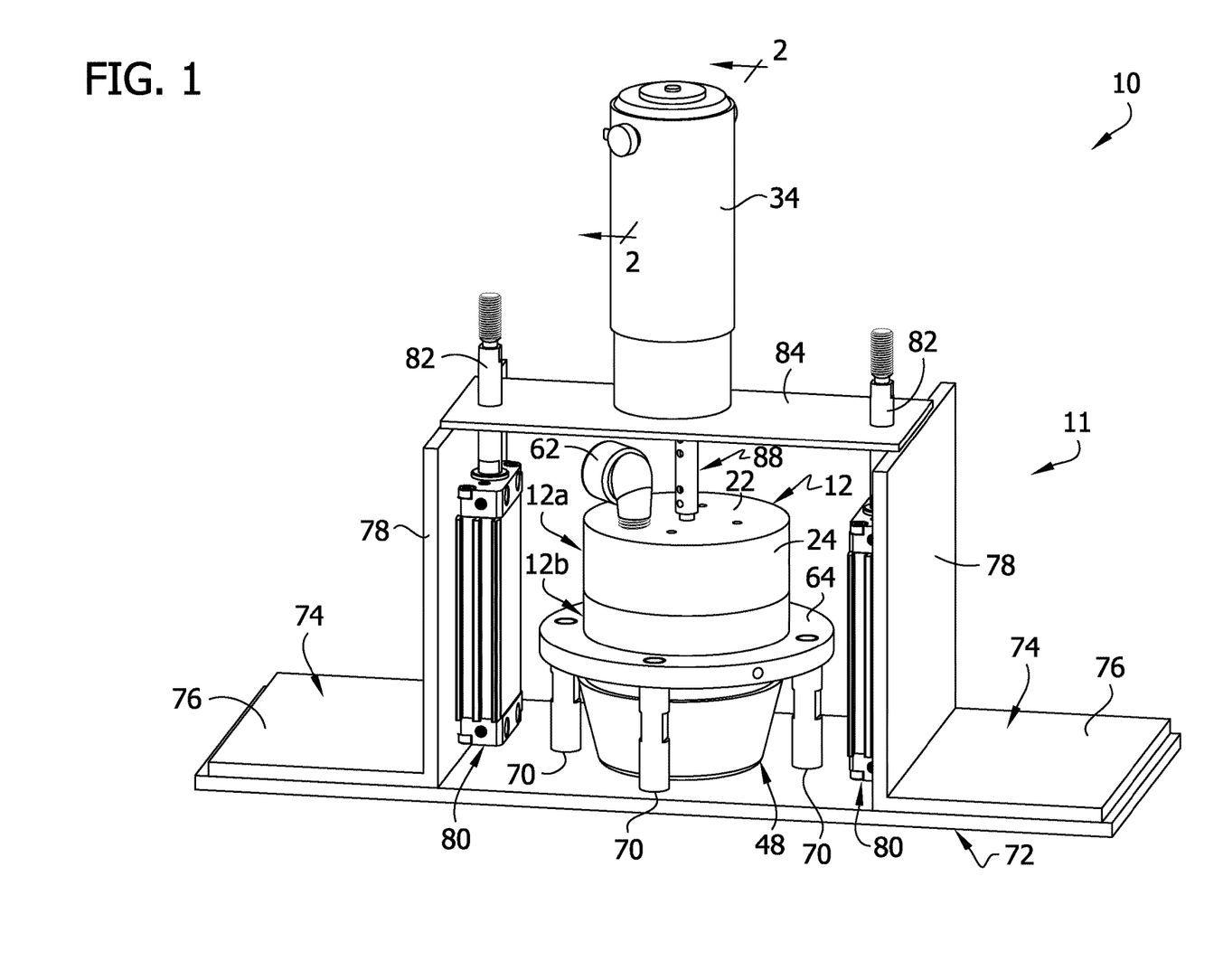
FIG. 1 is a perspective of a grease testing device.

Referring to FIG. 1, one embodiment of a grease testing device for testing oil separation from a grease sample is generally indicated at reference numeral 10. As explained in more detail below, the grease testing device 10 receives a grease sample and then shears or works the grease sample in order to determine the amount of oil separation from the grease sample.

Figure 2:
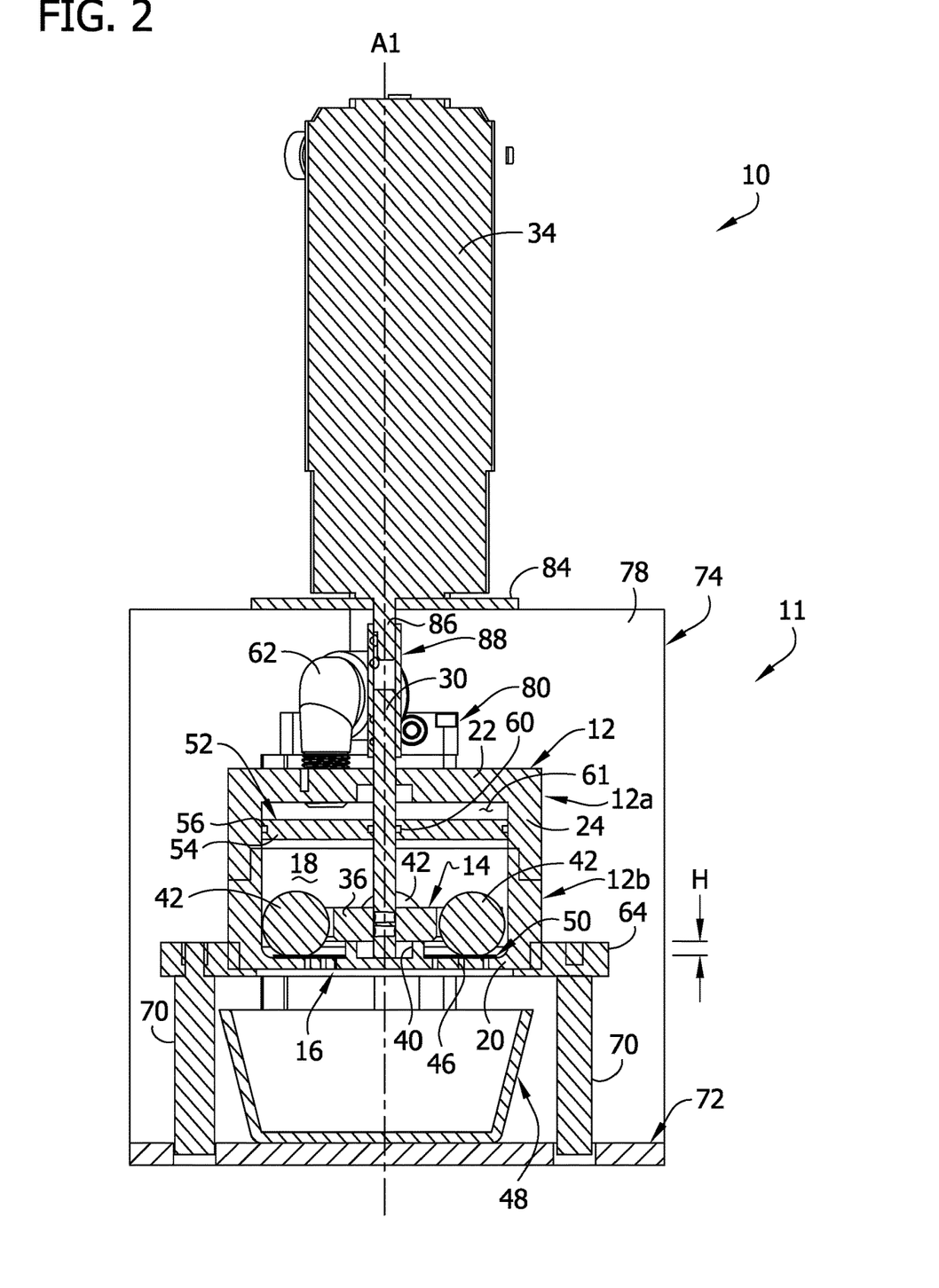
FIG. 2 is a cross-section of the grease testing device taken through line 2-2 of FIG. 1.
Figure 3:
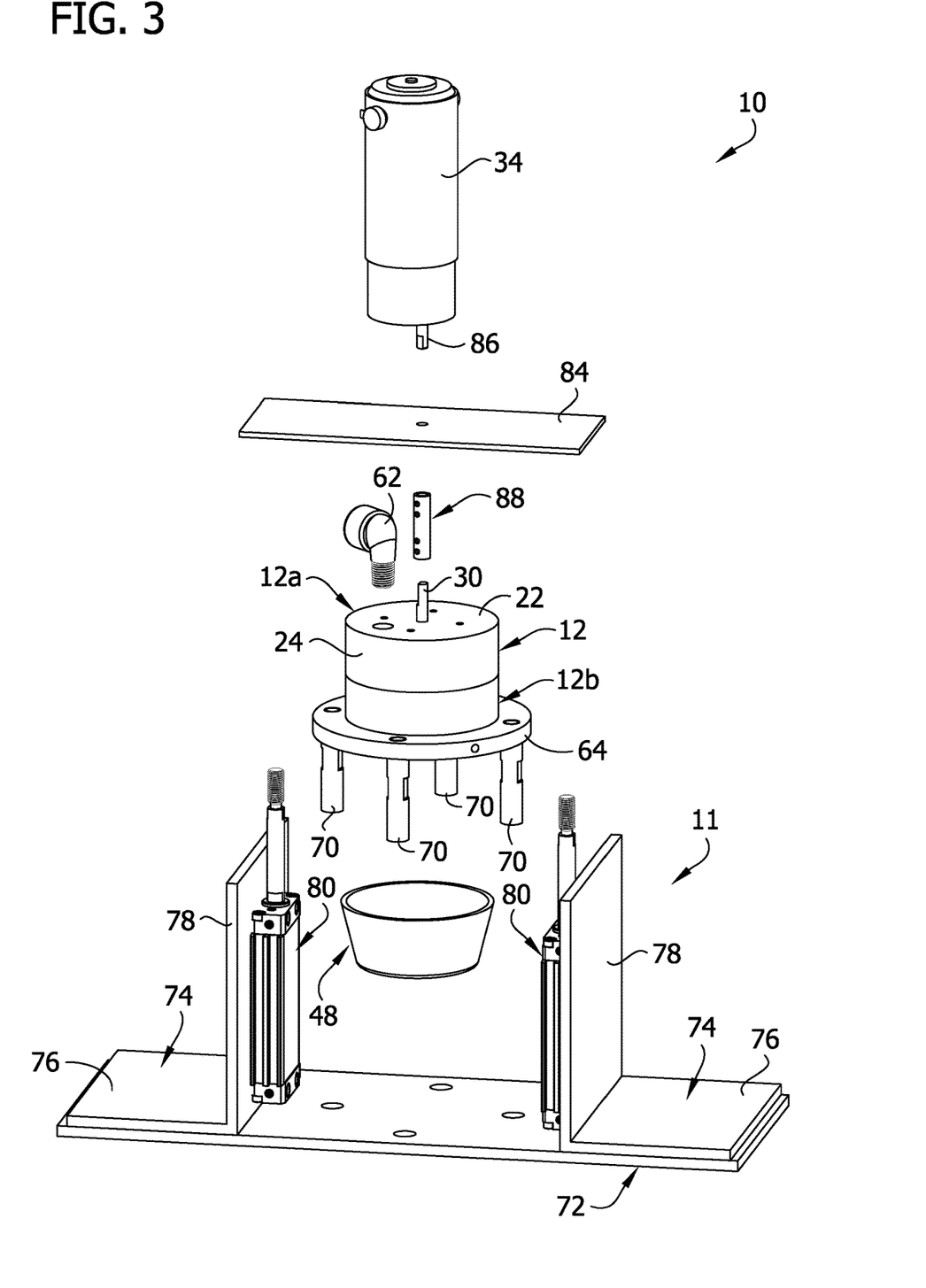
FIG. 3 is an exploded view of the grease testing device.

Referring to FIGS. 1-5, the grease testing device 10 includes a frame, generally indicated at 11, a container, generally indicated at 12, a grease shearer, generally indicated at 14 (FIG. 2), and a drain, generally indicated at 16 (FIG. 2). The frame 11 serves as a support for the container 12 and grease shearer 14, as well as other components of the testing device 10. As explained in more detail below, at least a portion of the grease shearer 14 moves within a compartment 18 of the container 12 to shear a grease sample contained therein. The drain 16 is arranged with respect to the compartment 18 to receive oil separated from the grease sample.

The container 12 defines the compartment 18 that receives the grease sample. The container 12 includes a lower plate 20, an upper plate 22, and a side wall 24 extending between and interconnecting the upper and lower plates. The compartment 18 is enclosed by the lower and upper plates 20, 22 and side wall 24. The side wall has a generally cylindrical shape and the upper and lower plates 22, 20 are generally circular. The container 12 can be selectively opened and closed to provide access to the compartment 18. In the illustrated embodiment, the container 12 has an upper portion 12a and a lower portion 12b that are releasably secured to one another with fasteners (not shown). The upper portion 12a includes the upper plate 22 and an upper section of the side wall 24. The lower portion 12b includes the lower plate 20 and a lower section of the side wall 24. The upper and lower sections of the side wall 24 define corresponding fastener openings 26 (FIG. 5) that are alignable and receive fasteners (e.g., screws) to releasably secure the upper and lower portions 12a, 12b of the container 12 together. Other fasteners such a clamps, etc. can be used without departing from the scope of the present invention. As shown in FIG. 2, the upper and lower sections of the side wall 24 overlap one another when the upper and lower portions 12a, 12b of the container 12 are connected to one another to create a leak proof seal therebetween. A gasket (not shown) can be provided between the upper and lower sections of the side wall 24 at the joint of the upper and lower portions 12a, 12b.

The grease shearer 14 of the grease testing device 10 is at least partially positioned in the compartment 18. The grease shearer 14 is configured to move in the compartment 18 to shear the grease sample housed in the compartment. In the illustrated embodiment, a portion of the grease shearer 14 is configured to rotate within the compartment 18 to shear the grease. The grease shearer 14 includes a drive shaft 30 that extends through a drive shaft opening 32 defined by the upper plate 22 and into the compartment 18. The drive shaft 30 and upper plate 22 may sealingly engage each other (or have an O-ring therebetween) to create a leak proof seal therebetween. while permitting the drive shaft to rotate within the drive shaft opening 32. The drive shaft 30 defines an axis A1 about which the grease shearer 14 rotates. The upper end of the drive shaft 30 is operatively connected to a motor 34 of the grease testing device 10, as explained in more detail below. The motor 34 is configured to move (e.g., rotate) the grease shearer 14 in the compartment 18 to shear the grease sample. In the illustrated embodiment, the motor 34 is an electric motor. Any type of electric motor or other type of motor can be used without departing from the scope of the present invention.

The grease shearer 14 includes a guide 36 (e.g., guide plate) disposed in the compartment 18. The guide 36 is vertically spaced apart from the lower plate 20 by a height H extending between an upper surface of the lower plate and a lower surface of the guide. The guide 36 is secured to the drive shaft 30 such that rotation of the drive shaft rotates the guide about the axis A1. In the illustrated embodiment, the guide 36 is releasably secured to the drive shaft 30 by a pair of set screws (not shown), although other ways of securing the drive shaft to the guide can be used without departing from the scope of the present invention. The drive shaft 30 extends through a drive shaft opening 38 defined by the guide 36. In the illustrated embodiment, the drive shaft 30 extends vertically through the compartment 18 such that the lower end of the drive shaft engages and is support by the lower plate 20 of the container 12. In the illustrated embodiment, the guide 36 is generally disc shaped. The guide 36 is sized and shaped such that a small clearance exists between a circumferential edge of the guide and an inner surface of the side wall 24 to permit the guide to rotate in the compartment 18. The container 12 may include a support wall 40 extending upward from the lower plate 20 and engaging the guide 36. The support wall 40 has a cylindrical shape extending around the axis A1. The support wall 40 supports the guide 36 and maintains the height H between the guide and the lower plate 20.

The grease shearer 14 includes at least one roller 42 configured to roll in the compartment 18 when the motor 34 moves the grease shearer. As explained in more detail below, rolling the roller 42 through the grease sample held in the compartment 18 shears the grease sample. The grease shearer 14 may include multiple rollers 42. For example, in the illustrated embodiment, the grease shearer 14 includes four rollers 42, although more or fewer rollers can be used without departing from the scope of the present invention. In the illustrated embodiment, the rollers 42 are provided in the form of ball bearings. The guide 36 is configured to move the rollers 36 within the compartment 18. Each roller 42 is positioned in a roller recess 44 in the guide 36. Each roller recess 44 has a generally U-shape that extends radially inward (e.g., toward the axis A1) from the circumferential edge of the guide 36. As shown in FIG. 2, when the rollers 42 are positioned in the roller recesses 44, each roller is spaced radially from the axis A1 and is adjacent the side wall 24. The rollers 42 are free to roll in any direction within the roller recess 44. As explained in more detail below, when the guide 36 is rotated by the motor 34, the guide contacts and moves (e.g., pushes) the rollers about the vertical axis A1. The rollers 42 are supported by and engage the lower plate 20. The arrangement is such that the rollers 42 are captured in the roller recesses 44 by the guide 36, the lower plate 20, and the side wall 24. Desirably, the height H between the guide 36 and the lower plate 20 is such that the guide at the roller recesses 44 extends above and below the heightwise midpoint of the rollers 42. In one embodiment, the rollers 42 are made from a metal, such as stainless steel, and have a diameter of about ¾ inches (about 1.9 cm).

Other grease shearers can be used without departing from the scope of the present invention. For example, other numbers and/or types of rollers can be used. Moreover, rollers can be omitted such that the grease is sheared without rolling.

Figure 4:
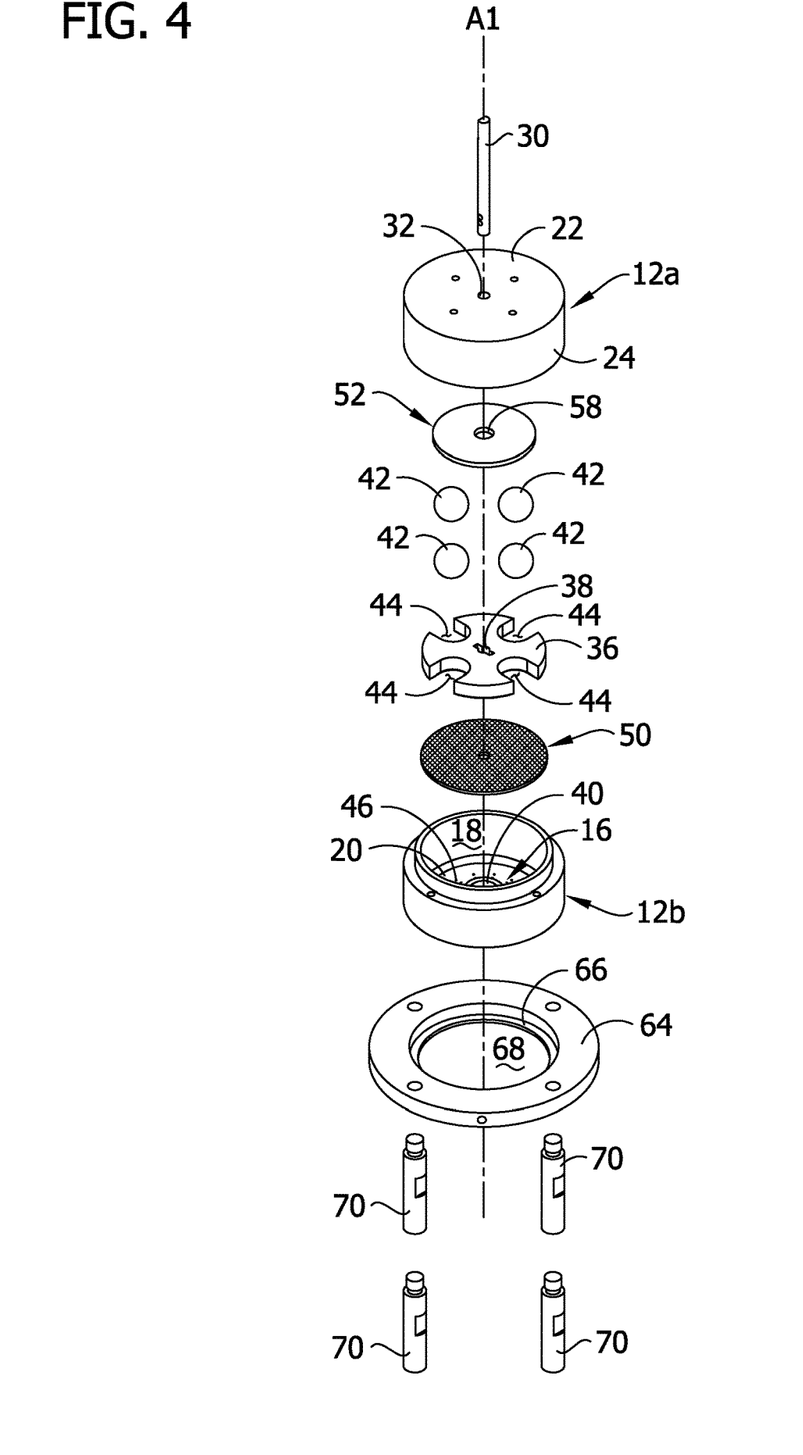
FIG. 4 is an enlarged, exploded view of a container of the grease testing device showing internal components.
Figure 5:
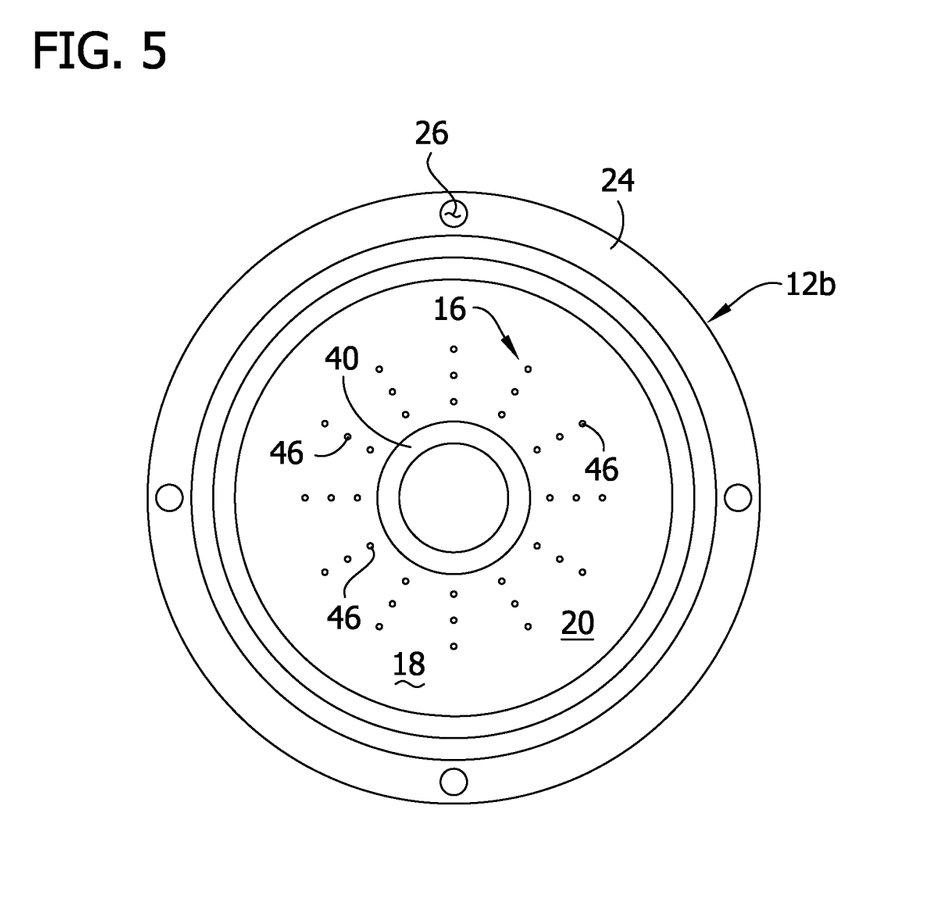
FIG. 5 is a top view of a lower portion of the container of the testing device.

Referring to FIGS. 2, 4 and 5, the drain 16 of the grease testing device 10 is located at the bottom of the compartment 18. The drain 16 is configured to keep the grease sample in the compartment 18 but permit oil that separates from the grease sample to exit the compartment by gravity. The drain 16 includes a plurality of drain openings 46 in the lower plate 20 of the container 12. The drain openings 46 extend through the lower plate 20. The drain openings 46 are in fluid communication with the compartment 18. The arrangement is such that oil that separates from the grease sample in the container 12 can flow, under the influence of gravity, into the drain openings 46 out of the compartment 18. The illustrated drain openings 46 have a diameter of about 1/32 inches (0.8 mm). The drain openings 46 are spread out over the lower plate 20 in an array and are positioned generally below the rollers 42. The drain 16 also includes a screen 50 (broadly, "filter") arranged to cover the drain openings 46. The screen 50 is configured to permit the oil that separates from the grease sample to pass through the screen and into the drain openings 46 but prevent the grease sample from passing through the drain openings. The screen 50 has screen openings that are smaller than the drain openings 46. Desirably, the screen openings have a size in the inclusive range of 0.012 inches (0.3 mm) to 0.0012 inches (0.03 mm), or more desirably in the inclusive range of 0.009 inches (0.2 mm) to 0.0035 inches (0.09 mm). The screen 50 may have a mesh size in the inclusive range of 40 mesh to 500 mesh. The small screen openings permit the oil to pass through the screen but hinder the grease sample from passing through. Desirably, the screen 50 is positioned over lower plate 20 and the drain openings 46 to prevent the grease sample from clogging the drain openings 46. Accordingly, the rollers 42 may engage and roll on the screen 50.

Drains having other configurations can be used without departing from the scope of the present invention. For example, other types and numbers of drain openings can be used, as well as other types of screens. The screen can be omitted. Moreover, the drain can include one or more drain tubes for collecting oil from the grease compartment.

The grease testing device 10 includes an oil collection reservoir 48 positioned to collect the oil from the drain 16. Specifically, the oil collection reservoir 48 is positioned below the drain openings 46 so that the oil falls into the oil collection reservoir after the oil flows through the drain openings. In the illustrated embodiment, the oil collection reservoir is an open top cup.

Referring to FIGS. 2 and 4, the grease testing device 10 may also include a piston 52 arranged to reduce a volume of the compartment 18. As explained in more detail below, the piston 52 is configured to move in the compartment 18 to pressurize the grease sample (or at least reduce air pockets) in the compartment. The piston 52 includes a piston head 54 positioned in the compartment 18 between the upper and lower plates 22, 20. The piston head 54 is disposed above the rollers 42 and guide 36 of the grease shearer 14. The piston head 54. The piston head 54 is generally disk shaped. The piston head 54 includes a circumferential groove 56 that receives a sealing element (not shown), such as an O-ring or gasket, to form a leak proof seal between the piston head and the side wall 24. The piston head 54 also defines a drive shaft opening 58 through which the drive shaft 30 extends. The piston head 54 can slide longitudinally along the drive shaft 30 to change the volume of the compartment 18. The piston head 54 includes a groove 60 surrounding the drive shaft opening 58 in which a gasket is receivable for sealingly engaging the drive shaft 30 to create a leak proof seal. In the illustrated embodiment, the seal between the drive shaft 30 and the piston head 54 permits the piston head to move along the drive shaft without breaking the seal.

In the illustrated embodiment, the piston 52 divides an interior of the container into the grease compartment 18 and into an upper compartment 61 between the upper plate 22 and the piston head 54. As explained in more detail below, the upper compartment 61 (broadly, "piston chamber") receives gas to move the piston head 54 downward to reduce the volume of the lower compartment and optionally pressurize the grease sample held in the lower compartment. A fitting 62 is threadably coupled to the upper plate 22 and is fluidly connected to the upper compartment 61. The fitting 62 is configured (e.g., has a threaded inlet) to attach to a fluid line (not shown) to fluidly connect the upper compartment to a source of pressurized gas (not shown), such as an air compressor. The pressure source supplies the compressed gas to the compartment 61 to move the piston head 54.

Referring to FIGS. 1-4, the frame 11 of the grease testing device 10 includes a support ring 64 (broadly, "receiver") configured to removably receive and support the container 12 in an elevated position. The support ring 64 includes a lip 66 that extends around a container opening 68 defined by the support ring. The lip 66 engages and supports the container 12 when the container is removably inserted into the container opening 68. Desirably, the support ring 64 forms a friction fit with the container 12 to prevent the container from moving within the container opening 68 when a grease sample is being tested. When the container 12 is supported by the support ring 64, the container opening 68 is aligned with the drain 16 (e.g., drain openings 46) to permit the oil separated from the grease sample to flow into the oil collection reservoir 48 through the container opening. Thus, the support ring 64 supports the container 12 in an elevated position that is above the oil collection reservoir. A plurality of posts 70 (broadly, "support structure") are secured to the support ring 64 and hold the support ring in the elevated position defining a receiving space for the reservoir below the drain. The supports 70 are spaced apart on the support ring 64 circumferentially to provide space for the oil collection reservoir 48 to pass through to allow an operator to install and remove the oil collection reservoir below the container 12.

The frame 11 of the grease testing device 10 includes a base 72 configured to rest on a support surface (not shown), such as a table top. The base 72 supports the various components of the grease testing device 10. For example, the supports 70 are secured to the base 72 to position the support ring 64 and container 12 in an elevated position above the base. Similarly, the oil collection reservoir 48 rests on and is supported by the base 72. The frame 11 further includes opposite support brackets 74 secured to the base 72. In the illustrated embodiment, the support brackets 74 are L-shaped with a horizontal flange 76 secured to the base 72 and a vertical flange 78 extending upward from the base. Two actuators 80 are secured to respective vertical flanges 78 of the support brackets 74. The actuators 80 are operatively connected to the motor 34 by a motor support 84. Each actuator 80 includes a linearly movable rod 82. In the illustrated embodiment, the motor support 84 comprises a plate connected to and extending between the rods 82 of the actuators 80. The motor support plate 84 can be connected to the rods 82 by any suitable means, such as with nuts (not shown) threadably received on the rods. The motor 34 is secured to the motor support plate 84 and is positioned thereon such that a motor shaft 86 of the motor 34 is aligned with the axis A1 of the drive shaft 30. An actuator switch (not shown) can be operatively connected to the actuators 80 to control the movement of the actuators. Similarly, a motor switch (not shown) can be operatively connected to the motor 34 to control the movement of the motor. In one embodiment, a controller (not shown) is operatively connected to the actuators 80 and/or motor 34 to control the movement thereof. In this embodiment, the controller may be connected to the motor and/or actuator switches. In one embodiment, the controller is configured (e.g., programmed) to keep track of the run time of the motor 34 and includes a display (not shown) to display the run time to an operator. In yet another embodiment, the testing device 10 can include a scale on which the reservoir 48 is supported for measuring the weight of the oil collected by the reservoir. The scale can be operatively connected to the controller to monitor the weight of the oil over time, such as at intervals during a grease test.

The actuators 80 (broadly, at least one actuator) are configured to move the motor 34 between an operational position (FIG. 1) and an access position (not shown). In the operational position, the motor 34 is positioned to move the grease shearer 14. Specifically, in the operational position, the motor shaft 86 is adjacent the drive shaft 30 of the grease shearer 14 so that a coupling 88 can extend between and connect the two components together. The coupling 88 operatively connects the motor shaft 86 to the drive shaft 30 so that the two components rotate conjointly. The coupling 88 is a tubular shaft or sleeve that extends over the upper end of the drive shaft 30 and lower end of the motor shaft 86. Set screws (not shown) releasably secure the coupling 88 to the drive shaft 30 and motor shaft 86. Accordingly, the coupling 88 operatively connects the motor 34 to the grease shearer 14 so that the motor can move the grease shearer 14 in the compartment 18. As shown in FIG. 1, in the operational position, the motor support plate 84 engages and rests on upper ends of the support brackets 74.

In the access position, the motor 34 is positioned to permit access to the grease compartment. Specifically, in the access position, the motor 34 is raised to a position above the operational position by the actuators 80 to provide the necessary space above the container 12 to permit the operator to access and/or remove the container from the support ring 64. Thus, when the motor 34 is in the access position, the operator can remove the container 12 from the support ring 64, fill the container 12 with a grease sample and then place the container back on the support ring. The actuator switch (not shown) and/or controller are operatively coupled to the actuators 80 to control the movement of the motor 34 between the operational and access positions. Before raising the motor 34, set screws in the coupling 88 are removed to permit the motor shaft 86 to separate from the drive shaft 30.

Other ways of supporting and/or positioning the motor 34 can be used without departing from the scope of the present invention. For example, frames having other configurations can be used, and motor movement mechanisms having other configurations can be used.

The various components of the grease testing device 10, particularly the components that come into contact with the grease sample (e.g., container 12, grease shearer 14, etc.) are releasably connected to one another. This allows an operator to disassemble the components and clean the components.

In operation, the grease testing device 10 can be used to test a grease sample for oil separation. To test a grease sample, the operator first weighs the grease testing device 10, without the oil collection reservoir 48, on a scale (not shown) to obtain a weight of the device without the reservoir. Then the operator loads grease to be tested. To do this, the operator loosens the set screws (not shown) on the coupling device 88 and moves the motor 34 to the access position. The operator removes the container 12 from the support ring 64 and separates the upper and lower portions 12a, 12b of the container 12 from one another to access the compartment 18. A grease sample is then placed in the compartment 18, specifically in the portion of the compartment defined by the lower portion 12b of the container 12. The grease shearer 14 may be already positioned in the compartment 18 or inserted therein after the grease sample is placed in the compartment. The grease sample surrounds the rollers 42 and guide 36 of the grease shearer 14. The operator then reconnects the upper and lower portions 12a, 12b of the container 12 together to enclose the compartment 18, making sure the drive shaft 30 of the grease shearer 14 extends through the upper plate 22. The container 12 is then placed back on the support ring 64. The operator moves the motor 34 to the operational position and tightens the set screws on the coupling device 88 to connect the motor to the grease shearer 14. The operator then weighs the grease testing device 10 on the scale to obtain a first or pre-test weight of the device with the grease sample contained therein.

After the grease testing device 10 is weighed, the operator positions the oil collection reservoir 48 on the base 72 beneath the drain 16. The piston is operated to move the piston head to remove air pockets in the grease sample and optionally to pressurize the grease sample (e.g., 1-10 psi, or 1-6 psi, such as about 5 psi). To start the test, the operator turns on the motor 34 with the motor switch (not shown) to move the grease shearer 14 within the compartment 18. The motor 34 rotates the drive shaft 30, guide 34 and rollers 42 within the compartment 18. Desirably, the motor 34 rotates at a rotational rate in the inclusive range of about 60 to 80 RPM. As the rollers 42 are pushed along by the guide 36 and roll over the screen 50 on the lower plate 20, the rollers shear or work the grease sample. This mechanical action by the grease shearer 14 causes the thickener, specifically the solid particles or fibers, in the grease sample to break down. As the thickener breaks down, the thickener releases some of the oil (e.g., separated oil) in the grease sample. It will be appreciated that some of the oil may naturally separate from the thickener as well. This separated oil flows out of the compartment 18 through the drain 16 and into the oil collection reservoir 48 which collects the separated oil. The screen 50 permits the separated oil to pass through while keeping the grease sample in the compartment to be sheared by the grease shearer 14.

The movement of the rollers 42 mimics the mechanical action (e.g., movement) of ball bearings in a bearing of a machine that is lubricated by the grease. Thus, by shearing the grease sample with the grease shearer 14, the grease testing device 10 is able to replicate the working conditions experienced by the grease in a machine. As a result, a more accurate approximation of the oil separation in a grease under working conditions is provided, permitting a more accurate determination about how the grease will perform when used to lubricate a machine.

The motor 34 is run for a set period of time (broadly, a shearing duration) to continuously shear the grease sample. In one embodiment, the controller may stop the motor 34 after a set period of time is reached and/or alert the operator after the set period of time is reached. For example, the motor 34 can be run for a period of time in the inclusive range of about 10 minutes to about 80 hours. The length of the time the motor 34 is run may depend on the type of grease and/or the type of lubrication system used in the field to deliver the grease in the particular application. For example, a lubrication system may be designed to replenish grease in a bearing every hour. Accordingly, in the test, the operator may run the motor 34 for an hour to determine the amount of oil separation the grease would experience in the machine before fresh grease is added. In other words, the operator may run the motor 34 for the amount of time the grease is expected to lubricate the parts of a machine (which may also include any time spent in a lubrication system as well). After the motor 34 runs for the set period of time, the motor is turned off, which can be done manually or by the controller. The operator removes the oil collection reservoir 48 and weighs the grease testing device 10 on the scale to obtain a second or post-test weight of the device with the grease sample contained therein minus the separated oil.

Optionally, while the motor 34 is moving the grease shearer 14, the pressure source (not shown) is supplying a compressed gas to the upper compartment 61, via the fitting 62. The compressed gas moves the piston head 54 downward along the drive shaft 30 to reduce the volume of the grease compartment 18, which holds the grease sample. As a result, the piston head 54 engages and optionally pressurizes the grease sample, pushing the grease sample into contact with the grease shearer 14, specifically the rollers 42. As the grease shearer 14 moves within the compartment 18, voids may form within the grease sample around the grease shearer, reducing the effectiveness of the grease shearer. Accordingly, the piston 52 applies pressure to the grease sample to push the grease sample into contact with the shearer and reduce voids. The piston may pressurize the grease sample to a pressure in the inclusive range of about 5 to 1,000 psi (about 34 to 6900 kpa), or more desirably in the inclusive range of about 5 to 30 psi (about 34 to 210 kpa). The pressure can be used to simulate conditions in a field environment in which the grease will be used and/or for simulating long term oil separation in a shorter duration test.

In addition, during the test (e.g., while the motor 34 is running), the grease testing device 10 may be placed within an oven (not shown) to heat the grease sample. For example, the grease can be heated to a temperature in the inclusive range of 70 to 130 degrees F. (21 to 55 degrees C.). The heat can simulate heat in a field environment in which the grease will be used and/or for simulating long term oil separation in a shorter duration test. Heat and/or pressure, or neither, may be used.

To determine the results of the test, the operator compares the weight (broadly, an amount) of the grease sample to a weight (broadly, an amount) of the oil separated from the grease. Specifically, the operator subtracts the device weight from the first and second weights to obtain a pre-test weight of the grease sample and a post-test weight of the grease sample, respectively. The operator then compares (e.g., subtracts) the pre-test and post-tests weights to determine the amount (e.g., weight) of oil that separated from the grease sample. The weight of the separated oil is then compared to (e.g., divided by) the pre-test weight of the grease to determine an oil separation value for the grease sample. The oil separation value can be expressed as a percentage that reflects the difference or reduction in weight by the grease sample as a result of the oil separating. For example, a grease sample with an oil separation value equal to or less than 5% indicates the grease sample retained a sufficient amount of oil to maintain lubrication. A grease sample with an oil separation value between 5% and 10% is acceptable. A grease sample with an oil separation value equal to or greater than 10% indicates the grease sample did not retain a sufficient amount of oil and, thus, would not maintain lubrication. In other words, an oil separation value equal to or greater than 10% indicates there is not enough oil remaining in the grease to form a sufficient hydrodynamic film of oil between the moving parts in the machine to prevent direct contact. Other methods for determining the oil separation value of the grease sample using the grease testing device 10 can be used without departing from the scope of the present invention. For example, the operator may, instead of weighing the grease testing device 10 after the test, weigh the oil collection reservoir 48 with the separated oil contained therein and subtract the weight of the reservoir to determine the amount of oil separated from the grease sample.

In addition, the grease testing device 10 can be used to determine the oil separation rate of the grease sample. For example, the operator can periodically weigh the grease testing device 10 or the oil collection reservoir 48, as described above, during the test (e.g., determine the weight at set intervals within the overall duration of the test). Accordingly, the operator can determine oil separation values (e.g., intermediate oil separation values) at these intervals, as described above. The operator can then compare the intermediate oil separation values with the time they were taken to determine the oil separation rate of the grease sample. Such information can then be used to determine the point in time at which the grease sample will no longer provide acceptable levels of lubrication. For example, if a grease sample has intermediate oil separation values of 2.6%, 4.8%, 8.7%, and 10.9% at one hour intervals during a test, the operator knows the grease sample will no longer provide an acceptable level of lubrication at some point between hours 3 and 4—the point at which the oil separation value became greater than 10%. This information can then be used to determine how often the grease of this particular type needs to be replenished in order to provide continuous, acceptable levels of lubrication. Accordingly, using this information, grease lubrication systems can be optimized to minimize the amount of grease distributed to a machine while still providing an acceptable level of lubrication (e.g., wait the maximum period of time before replenishing the grease).

The grease testing device 10 can also be used to test the compatibility of different types of greases that are mixed together to form a grease combination. Two or more different types of greases are considered compatible when the amount or rate of oil separation in the grease combination is equal to or less than the amount or rate of oil separation in the greases individually. By using the grease testing device 10 to determine the separation values and/or separation rates of the individual greases and the grease combination and then comparing the values, the compatibility of individual grease types can be determined.

Figure 6:
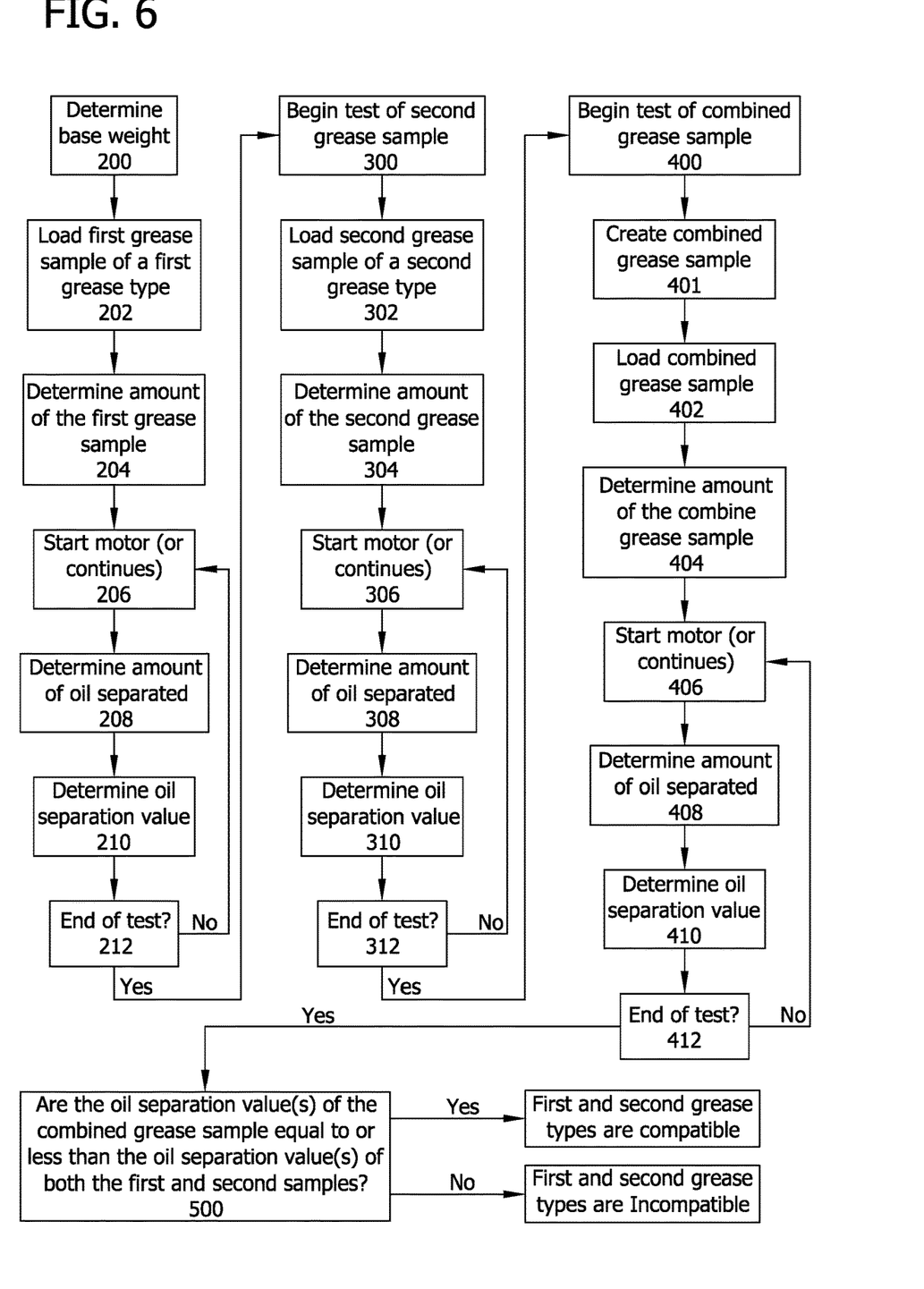
FIG. 6 is a flow diagram of method steps for testing greases and testing compatibility of greases.

FIG. 6 is a flow diagram of one embodiment of a method of using the grease testing device 10 to determine the compatibility of the individual greases (broadly, perform a grease separation test). At 200, the operator determines the device weight of the grease testing device 10 without the oil collection reservoir 48. At 202, the operator loads a first grease sample of a first grease type into the container 12 of the grease testing device 10. At 204, the amount of the first grease sample is determined by comparing the weight of the grease testing device 10 with the first grease sample to the device weight, as described above. At 206, the operator starts the motor 34 to start shearing the first grease sample with the grease shearer 14. The motor runs continuously for a first shearing duration (e.g., preset period of time) to continuously shear the first grease sample. The first shearing duration can be an interval duration for the test or the first shearing duration can be the entire duration of the test, depending on if the operator wants to determine the oil separation rate and/or the amount of oil separation, respectively. At 208, the first shearing duration concludes and the operator determines the amount of oil separated from the first grease sample. This can be done by weighing the grease testing device 10 or the oil collection reservoir 48, as described above. The motor 34 may be stopped to determine the amount of oil separated from the first grease sample or continue to run during this time. At 210, the operator determines the first oil separation value of the first grease sample for the first shearing duration. This is done by comparing the amount of the first grease sample to the amount of the oil separated, as described above. At 212, the operator determines if the grease separation test for the first grease sample is finished. For example, if the first shearing duration was the duration of the entire test, the grease separation test for the first grease sample is complete and the operator proceeds to step 300. However, if a grease separation rate for the first grease sample is being determined, the first shearing duration was the first duration interval of the grease separation test. Accordingly, the test is not complete and the grease separation test returns to 206 to continue to shear the first grease sample for a subsequent, second shearing duration (e.g., interval) to determine a second oil separation value at 210. This process repeats for additional subsequent shearing durations (e.g., third, fourth, fifth, etc. shearing durations) to determine subsequent oil separation values (e.g., third, fourth, fifth, etc. oil separation values) until the complete duration (e.g., time) of the test has been reached. Then the operator may determine the oil separation rate of the first grease sample using the oil separation values. Once the grease separation test for the first grease sample has ended, the test proceeds to 300. If an operator was only testing the oil separation for a single sample of grease, and not determining grease compatibility, the testing process is finished with a yes at 212.

At 300, a grease separation test for a second grease sample begins. At this time, the first grease sample is removed from the container 12 of the grease testing device 10. The second grease sample is of a second grease type that is different than the first grease type. The test of the second grease sample is the same as the test for the first grease sample. Thus, for ease of comprehension, where the same steps are used, reference numerals "100" units higher are employed. After the oil separation value(s) and/or oil separation rate for the second grease sample have been determined, the test for the second grease sample has ended and the test proceeds to 400.

At 400, a grease separation test for a grease combination or combined grease sample begins. At this time, the second grease sample is removed from the container 12 of the grease testing device. The combined grease sample is a mixture of the first and second grease types. At 401, the operator creates the combined grease sample by mixing together samples of the first and second grease types. The mixture can include equal parts of the grease types or unequal parts. After the combined grease sample is formed, the remaining steps for the test of the combined grease sample are the same as the test for the first grease sample. Thus, for ease of comprehension, where the same steps are used, reference numerals "200" units higher are employed. After the oil separation value(s) and/or oil separation rate for the combined grease sample have been determined, the test for the combined grease sample has ended and the test proceeds to 500.

At 500, the operator compares the oil separation value(s) and/or oil separation rates of the combined grease sample to the oil separation value(s) and/or oil separation rates (e.g., separation values at time intervals) of the first and second grease samples. If the oil separation value(s) and/or oil separation rates of the combined grease sample are equal to or less than the corresponding oil separation value(s) and/or oil separation rates of both the first and second grease samples, the first and second grease types are compatible with one another. If the oil separation value(s) and/or oil separation rates of the combined grease sample are greater than the corresponding oil separation value(s) and/or oil separation rates of either of the first or second grease samples, the first and second grease types are incompatible with one another. Other methods of testing the compatibly of greases using the grease testing device 10 can be used without departing from the scope of the present invention. For example, it will be understood that the operator may only record the weights measured during the operation of the grease testing device 10 and then determine the amount/rates/values of oil separation after the grease separation device is no longer being used. Moreover, while the illustrated example only determines the compatibility of two grease types, it will be understood that the procedure can be modified to determine the compatibility of three or more grease types. In addition, the testing of the grease samples can occur in any order.

Modifications and variations of the disclosed embodiments are possible without departing from the scope of the invention defined in the appended claims. For example, where specific dimensions or values are given, it will be understood that they are exemplary only and other dimensions are possible.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. A grease testing device for testing oil separation from a grease sample, comprising:
   a container defining a grease compartment for holding the grease sample;
   a grease shearer at least partially positioned in the grease compartment and configured to move in the grease compartment to shear the grease sample in the grease compartment;
   a motor operatively connected to the grease shearer to move the grease shearer in the grease compartment to shear the grease sample; and
   a drain arranged with respect to the grease compartment to receive oil separated from the grease sample from the grease compartment.

2. The grease testing device of claim 1, wherein the grease shearer is configured to rotate in the grease compartment.

3. The grease testing device of claim 1, wherein the grease shearer includes at least one roller configured to roll in the grease compartment when the motor moves the grease shearer.

4. The grease testing device of claim 3, wherein the at least one roller comprises multiple rollers and the grease shearer further includes a guide rotatable by the motor to guide movement of the multiple rollers.

5. The grease testing device of claim 1, wherein the container includes a plurality of drain openings in fluid communication with the grease compartment, the drain openings forming at least a portion of the drain.

6. The grease testing device of claim 5, wherein the drain includes a filter having filter openings smaller than the drain openings, the filter arranged to cover the plurality of drain openings and configured to permit the oil from the grease sample to pass through the filter openings.

7. The grease testing device of claim 1, wherein the drain includes a filter having filter openings sized to permit the oil from the grease sample to pass through the filter openings.

8. The grease testing device of claim 1, further comprising an oil collection reservoir positioned to collect the oil from the drain.

9. The grease testing device of claim 1, further comprising a piston arranged to reduce a volume of the grease compartment.

10. The grease testing device of claim 9, wherein the piston includes a piston head, and the piston head is movable with respect to the grease compartment to pressurize the grease sample in the grease compartment.

11. The grease testing device of claim 10, wherein the piston includes a gasket carried by the piston head to form a grease seal at the piston head.

12. The grease testing device of claim 9, wherein the piston includes a piston chamber in which gas is receivable to move the piston head by gas pressure to reduce the volume of the grease compartment.

13. The grease testing device of claim 1, further comprising an actuator operatively coupled to the motor, the actuator configured to move the motor between an operational position and an access position, the motor in the operational position being located to move the grease shearer, and the motor in the access position being located to permit access to the grease compartment.

14. The grease testing device of claim 1, further comprising a base configured to rest on a support surface, the base supporting the container, the motor, and the grease shearer.

15. A method for testing a grease for oil separation, the method comprising:
   providing a first grease sample of a first grease type in a grease compartment;
   moving a grease shearer in the grease compartment for a first shearing duration to shear the first grease sample in the grease compartment;

collecting oil separated from the first grease sample from the grease compartment; and comparing an amount of the collected oil to an amount of the first grease sample to determine a first oil separation value of the first grease sample.

16. The method of claim 15, further comprising:

determining a weight of the first grease sample before shearing the first grease sample; and determining a weight of the collected oil;

wherein comparing the amount of the collected oil to the amount of the first grease sample comprises comparing the weight of the first grease sample to the weight of the collected oil.

17. The method of claim 15, further comprising:

moving the grease shearer in the grease compartment for a second shearing duration to further shear the first grease sample in the grease compartment;

collecting oil separated from the first grease sample from the grease compartment; and comparing an amount of the collected oil to an amount of the first grease sample to determine a second oil separation value of the first grease sample.

18. The method of claim 15, further comprising:

providing a combined grease sample in a grease compartment, the combined grease sample including grease of the first grease type and grease of a second grease type;

moving a grease shearer in the grease compartment for a first combined grease sample shearing duration to shear the combined grease sample in the grease compartment;

collecting oil separated from the combined grease sample from the grease compartment; and comparing an amount of the collected oil from the combined grease sample to an amount of the combined grease sample to determine a first oil separation value of the combined grease sample.

19. The method of claim 18, further comprising comparing the first oil separation value of the combined grease sample to the first oil separation value of the first grease sample to determine a compatibility of the first and second grease types.

20. The method of claim 18, further comprising:

moving the grease shearer in the grease compartment for a second combined grease sample shearing duration to further shear the combined grease sample in the grease compartment;

collecting oil separated from the combined grease sample from the grease compartment; and comparing an amount of the collected oil to an amount of the combined grease sample to determine a second oil separation value of the combined grease sample.

* * * * *